United States Patent
Tashino et al.

(10) Patent No.: US 6,670,497 B2
(45) Date of Patent: Dec. 30, 2003

(54) PHTHALIC DIESTER DERIVATIVES AND ELECTRON DONORS

(75) Inventors: Kunihiko Tashino, Kanagawa (JP); Yukihiro Suzuki, Kanagawa (JP); Isa Nishiyama, Kanagawa (JP); Hayashi Ogawa, Kanagawa (JP); Takuma Yoshida, Kanagawa (JP); Motoki Hosaka, Kanagawa (JP); Maki Sato, Kanagawa (JP)

(73) Assignee: Toho Titanium Co., Ltd., Chigasaki (JP)

( * ) Notice: Subject to any disclaimer, the term of this patent is extended or adjusted under 35 U.S.C. 154(b) by 0 days.

(21) Appl. No.: 09/926,802

(22) PCT Filed: Apr. 23, 2001

(86) PCT No.: PCT/JP01/03460
§ 371 (c)(1),
(2), (4) Date: Mar. 19, 2002

(87) PCT Pub. No.: WO01/81292
PCT Pub. Date: Nov. 1, 2001

(65) Prior Publication Data
US 2003/0036594 A1 Feb. 20, 2003

(30) Foreign Application Priority Data

| Apr. 24, 2000 | (JP) | 2000-122506 |
| Aug. 30, 2000 | (JP) | 2000-261620 |
| Sep. 29, 2000 | (JP) | 2000-298766 |

(51) Int. Cl.$^7$ .................................... C07C 69/76
(52) U.S. Cl. ............................... 560/76; 560/83
(58) Field of Search .............................. 560/76, 83

(56) References Cited

FOREIGN PATENT DOCUMENTS

| EP | 45976 | 2/1982 |
| EP | 363922 | 4/1990 |
| GB | 1422834 | 1/1976 |
| JP | 62-148450 | 7/1987 |
| JP | 63-72649 | 4/1988 |

OTHER PUBLICATIONS

Database CAPLUS on STN, Acc. No. 1987:213478, Chemische Berichte (1987), 120(5), p. 825–38 (abstract).*

* cited by examiner

*Primary Examiner*—Brian Davis
(74) *Attorney, Agent, or Firm*—Oblon, Spivak, McClelland, Maier & Neustadt, P.C.

(57) ABSTRACT

A phthalic acid diester derivative represented by a specific formula and an electron donor used in an olefin polymerization catalyst containing the phthalic acid diester derivative as an effective component. The electron donor can produce polymers with a high stereoregularity at an extremely high polymerization activity and high yield, and exhibit a high response to hydrogen.

19 Claims, No Drawings

PHTHALIC DIESTER DERIVATIVES AND ELECTRON DONORS

FIELD OF THE INVENTION

The present invention relates to an electron donor of an olefin polymerization catalyst, a novel phthalic acid diester derivative used as a plasticizer for resins such as vinyl chloride, a component for intermediates for the preparation of various compounds, and an electron donor used in the olefin polymerization catalyst containing the phthalic acid diester derivative.

BACKGROUND ART

Conventionally, phthalic acid diesters have been used as a common plasticizer for vinyl chloride. Diethyl phthalate, dibutyl phthalate, and di-iso-octyl phthalate are typical phthalic acid diesters. In the technology for polymerizing olefins, typically propylene, in the presence of a solid catalyst comprising magnesium and titanium as major components, an electron donor (an internal electron donor) is added to the solid catalyst to improve the stereoregularity of the formed polymer and the polymerization activity. A number of reports have proposed the use of specific phthalic acid esters as such an electron donor.

As a prior art using a phthalic acid diester as one of the components of the olefin polymerization catalyst, Japanese Unexamined Patent Publication No. (hereinafter referred to as JP-A) 63310/1982 and JP-A No. 63311/1982, for example, disclose a method of polymerizing olefins having three or more carbon atoms using a combined catalyst comprising a solid catalyst component containing a magnesium compound, titanium compound, and an electron donor such as a diester compound, e.g., phthalic acid ester, an organoaluminum compound, and an organosilicon compound having a Si—O—C linkage. JP-A 6006/1989 discloses a solid catalyst component for olefin polymerization containing an alkoxymagnesium, titanium tetrachloride, and dibutyl phthalate. The solid catalyst component was proven to be successful to some extent in producing a stereoregular propylene polymer at a high yield.

The polymers produced using these catalysts are used in a variety of applications including formed products such as parts of vehicles and household electric appliances, containers, and films. These products are manufactured by melting polymer powders produced by the polymerization and by forming the melted polymer using any one of various molds. In manufacturing formed products, particularly large products, by injection molding, melted polymers are sometimes required to have high fluidity (melt flow rate). Accordingly, a number of studies have been undertaken to increase the melt flow rate of polymers.

The melt flow rate greatly depends on the molecular weight of the polymers. In the polymer industry, hydrogen is generally used as a molecular weight regulator for polymers in the polymerization of olefins. In this instance, a large quantity of hydrogen is usually added to produce low molecular weight polymers which are the polymers having a high melt flow rate. However, the quantity of hydrogen which can be added is limited because of the pressure resistance of the reactor from the viewpoint of safety. In order to add a larger amount of hydrogen, the partial pressure of monomers to be polymerized has to be decreased. The decrease in the partial pressure, however, is accompanied by a decrease in the productivity. Additionally, use of a large amount of hydrogen may bring about a problem of cost. Development of a catalyst capable of producing polymers with a high melt flow rate by using a smaller amount of hydrogen, in other words, a catalyst which has a high activity to hydrogen or high response to hydrogen and which produces a highly stereoregular polymer at a high yield has therefore been desired. In the above-mentioned prior art, however, it is not sufficient to solve such a problem.

Accordingly, an object of the present invention is to provide a novel phthalic acid diester derivative useful as one of the components for an olefin polymerization catalyst, particularly a catalyst for the polymerization of propylene or ethylene, having a high response to hydrogen, which can produce polymers having high stereoregularity in an extremely high activity and high yield, and an electron donor used as an olefin polymerization catalyst containing the phthalic acid diester derivative as an effective component.

DISCLOSURE OF THE INVENTION

The present inventors have conducted extensive studies to solve the problems in conventional technologies relating to the catalysts for the polymerization of olefins. As a result, the present inventors have discovered a novel phthalic acid diester derivative which is extremely effective as an electron donor used as one of the components of such a catalyst. Confirmation of such an effect has led to the completion of the present invention.

Specifically, the above object is achieved in the present invention by a phthalic acid diester derivative of the following formula (1),

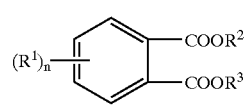

(1)

wherein $R^1$ is an alkyl group having 1 to 8 carbon atoms or a halogen atom; $R^2$ and $R^3$ may be either identical or different, representing an alkyl group having 1 to 12 carbon atoms; and n, which indicates the number of $R^1$, is 1 or 2, provided that when n is 2, the two $R^1$ groups may be either identical or different.

The above object is further achieved in the present invention by an electron donor used in a catalyst for the polymerization of olefins comprising a phthalic acid diester derivative of the above formula (1) as an effective component.

BEST MODE FOR CARRYING OUT THE INVENTION

In the phthalic acid diester derivative of the present invention, given as examples of the alkyl group having 1 to 8 carbon atoms represented by $R^1$ of the formula (1) are a methyl group, an ethyl group, a n-propyl group, an iso-propyl group, a n-butyl group, an iso-butyl group, a t-butyl group, a n-pentyl group, an iso-pentyl group, a neopentyl group, a n-hexyl group, an iso-hexyl group, a 2,2-dimethylbutyl group, a 2,2-dimethyl pentyl group, a iso-octyl group, and a 2,2-dimethylhexyl group. As halogen atoms represented by $R^1$, a fluorine atom, a chlorine atom, a bromine atom, and an iodine atom can be given. Of these groups represented by $R^1$, preferable groups are a methyl group, an ethyl group, a t-butyl group, a chlorine atom, a fluorine atom, and a bromine atom, with the methyl group, t-butyl group, chlorine atom, fluorine atom, and bromine atom being particularly preferable.

The groups represented by $R^2$ or $R^3$ include a methyl group, an ethyl group, a n-propyl group, an iso-propyl group, a n-butyl group, an iso-butyl group, a t-butyl group, a n-pentyl group, an iso-pentyl group, a neopentyl group, a n-hexyl group, an iso-hexyl group, a 2,2-dimethylbutyl group, a 2,2-dimethyl pentyl group, an iso-octyl group, a 2,2-dimethylhexyl group, a n-nonyl group, an iso-nonyl group, a n-decyl group, an iso-decyl group, and a n-dodecyl group. Of these, an ethyl group, a n-butyl group, an iso-butyl group, a t-butyl group, a neopentyl group, an iso-hexyl group, and an iso-octyl group are preferable, with an ethyl group, a n-butyl group, a neopentyl group, and an iso-hexyl group being particularly preferable.

The symbol n, which indicates the number of $R^1$, is 1 or 2, provided that when n is 2, the two $R^1$ groups may be either identical or different. When n=1, the substituent $R^1$ replaces the hydrogen atom at the 3, 4, or 5 position of the phthalic acid diester derivative, and when n=2, $R^1$ replaces the hydrogen atoms at the 4 and 5 positions.

Preferable phthalic acid diester derivatives are compounds having the structure of the formula (1), wherein n=1 or 2, $R^1$ is an alkyl group with 1 to 5 carbon atoms or a halogen atom, and $R^2$ and $R^3$ are alkyl groups with 4 to 8 carbon atoms including a tertiary carbon atom.

Specific examples of the compounds of the above formula (1), wherein n=1 or 2, $R^1$ is an alkyl group with 1 to 5 carbon atoms or a halogen atom, and $R^2$ and $R^3$ are alkyl groups with 4 to 8 carbon atoms including a tertiary carbon atom, include dineopentyl 3-methylphthalate, dineopentyl 4-methylphthalate, dineopentyl 3-ethylphthalate, dineopentyl 4-ethylphthalate, t-butylneopentyl 3-methylphthalate, t-butylneopentyl 4-methylphthalate, t-butyl neopentyl 3-ethylphthalate, t-butylneopentyl 4-ethylphthalate, dineopentyl 4,5-dimethyl phthalate, dineopentyl 4,5-diethyl phthalate, t-butyl dineopentyl 4,5-dimethylphthalate, t-butyl neopentyl 4,5-diethylphthalate,dineopentyl 3-fluorophthalate, dineopentyl 3-chlorophthalate, dineopentyl 4-chlorophthalate, dineopentyl 4-bromophthalate, and dineopentyl 4-t-butyl phthalate. Of these compounds dineopentyl 4-methylphthalate, dineopentyl 4,5-dimethylphthalate, dineopentyl 4-ethyl phthalate, dineopentyl 4,5-diethylphthalate, dineopentyl 4-bromophthalate, dineopentyl 3-fluorophthalate, and dineopentyl 4-t-butylphthalate are particularly preferable.

Specific examples of the compounds of the above formula (1), wherein n=2, one of the groups $R^1$ is a halogen atom and the other is an alkyl group with 1 to 8 carbon atoms, and at least one of the groups $R^2$ and $R^3$ is an alkyl group with 1 to 12 carbon atoms other than the alkyl group with 4 to 8 carbon atoms including a tertiary carbon atom include: diethyl 4-methyl-5-chlorophthalate, diethyl 4-methyl-5-bromo phthalate, diethyl 4-ethyl-5-chlorophthalate, diethyl 4-ethyl-5-bromophthalate, di-n-butyl 4-methyl-5-chlorophthalate, di-n-butyl 4-methyl-5-bromophthalate, di-n-butyl 4-ethyl-5-chlorophthalate, di-n-butyl 4-ethyl-5-bromophthalate, diisobutyl 4-methyl-5-chlorophthalate, diisobutyl 4-methyl-5-bromophthalate, diisobutyl 4-ethyl-5-chloro phthalate, diisobutyl 4-ethyl-5-bromophthalate, diisohexyl 4-methyl-5-chlorophthalate, diisohexyl 4-methyl-5-bromo phthalate, diisohexyl 4-ethyl-5-chlorophthalate, diisohexyl 4-ethyl-5-bromophthalate, diisooctyl 4-methyl-5-chloro phthalate, diisooctyl 4-methyl-5-bromophthalate, diisooctyl 4-ethyl-5-chlorophthalate, diisooctyl 4-ethyl-5-bromo phthalate, ethyl-n-butyl 4-methyl-5-chlorophthalate, ethyl-n-butyl 4-chloro-5-methyl phthalate, ethyl-n-butyl 4-methyl-5-bromophthalate, ethyl-n-butyl 4-bromo-5-methyl phthalate, ethyl-n-butyl 4-ethyl-5-chlorophthalate, ethyl-n-butyl 4-chloro-5-ethylphthalate, ethyl-n-butyl 4-ethyl-5-bromo phthalate, ethyl-n-butyl 4-bromo-5-ethylphthalate, ethyl isobutyl 4-methyl-5-chlorophthalate, ethylisobutyl 4-chloro-5-methylphthalate, ethylisobutyl 4-methyl-5-bromo phthalate, ethylisobutyl 4-bromo-5-methylphthalate, ethyl isobutyl 4-ethyl-5-chlorophthalate, ethyl isobutyl 4-chloro-5-ethylphthalate, ethylisobutyl 4-ethyl-5-bromophthalate, ethylisobutyl 4-bromo-5-ethylphthalate, ethylisohexyl 4-methyl-5-chlorophthalate, ethylisohexyl 4-chloro-5-methylphthalate, ethylisohexyl 4-methyl-5-bromophthalate, ethylisohexyl 4-bromo-5-methylphthalate, ethylisohexyl 4-ethyl-5-chlorophthalate, ethylisohexyl 4-chloro-5-ethyl phthalate, ethylisohexyl 4-ethyl-5-bromophthalate, ethyl isohexyl 4-bromo-5-ethylphthalate, n-butylisobutyl 4-methyl-5-chlorophthalate, n-butylisobutyl 4-chloro-5-methyl phthalate, n-butylisobutyl 4-methyl-5-bromophthalate, n-butylisobutyl 4-bromo-5-methyl phthalate, n-butylisobutyl 4-ethyl-5-chlorophthalate, n-butyl isobutyl 4-chloro-5-ethylphthalate, n-butylisobutyl 4-ethyl-5-bromophthalate, n-butylisobutyl 4-bromo-5-ethylphthalate, n-butylisohexyl 4-methyl-5-chlorophthalate, n-butylisohexyl 4-chloro-5-methylphthalate, n-butylisohexyl 4-methyl-5-bromo phthalate, n-butylisohexyl 4-bromo-5-methylphthalate, n-butyl isohexyl 4-ethyl-5-chlorophthalate, n-butylisohexyl 4-chloro-5-ethylphthalate, n-butylisohexyl 4-ethyl-5-bromophthalate, and n-butylisohexyl 4-bromo-5-ethylphthalate.

Specific examples of the compounds of the above formula (1), wherein n=1 or 2, $R^1$ is an alkyl group with 1 to 8 carbon atoms, and $R^2$ and $R^3$ are alkyl groups with 1 to 12 carbon atoms other than the alkyl group with 4 to 8 carbon atoms including a tertiary carbon atom include diethyl 3-methylphthalate, diethyl 4-methylphthalate, diethyl 3-ethylphthalate, diethyl 4-ethylphthalate, diethyl 3-t-butylphthalate, diethyl 4-t-butyl phthalate, diethyl 3-n-butylphthalate, diethyl 4-n-butylphthalate, diethyl 4,5-dimethylphthalate, diethyl 4,5-diethylphthalate, diethyl 4-methyl-5-ethylphthalate, diethyl 4-methyl-5-t-butylphthalate, diethyl 4-ethyl-5-t-butylphthalate, di-n-butyl 3-methylphthalate, di-n-butyl 4-methylphthalate, di-n-butyl 3-ethylphthalate, di-n-butyl 4-ethylphthalate, di-n-butyl 3-t-butylphthalate, di-n-butyl 4-t-butylphthalate, di-n-butyl 3-n-butylphthalate, di-n-butyl 4-n-butylphthalate, di-n-butyl 4,5-dimethylphthalate, di-n-butyl 4,5-diethylphthalate, di-n-butyl 4-methyl-5-ethyl phthalate, di-n-butyl 4-methyl-5-t-butylphthalate, di-n-butyl 4-ethyl-5-t-butylphthalate, diisobutyl 3-methyl phthalate, diisobutyl 4-methylphthalate, diisobutyl 3-ethyl phthalate, diisobutyl 4-ethylphthalate, diisobutyl 3-t-butyl phthalate, diisobutyl 4-t-butylphthalate, diisobutyl 3-n-butylphthalate, diisobutyl 4-n-butylphthalate, diisobutyl 4,5-dimethylphthalate,-diisobutyl 4,5-diethylphthalate, diisobutyl 4-methyl-5-ethylphthalate, diisobutyl 4-methyl-5-t-butylphthalate, diisobutyl 4-ethyl-5-t-butylphthalate, diisohexyl 3-methylphthalate, diisohexyl 4-methylphthalate, diisohexyl 3-ethylphthalate, diisohexyl 4-ethylphthalate, diisohexyl 3-t-butylphthalate, diisohexyl 4-t-butylphthalate, diisohexyl 3-n-butylphthalate, diisohexyl 4-n-butylphthalate, diisohexyl 4,5-dimethylphthalate, diisohexyl 4,5-diethyl phthalate, diisohexyl 4-methyl-5-ethylphthalate, diisohexyl 4-methyl-5-t-butylphthalate, diisohexyl 4-ethyl-5-t-butyl phthalate, diisooctyl 3-methylphthalate, diisooctyl 4-methyl phthalate, diisooctyl 3-ethylphthalate, diisooctyl 4-ethyl phthalate, diisooctyl 3-t-butylphthalate, diisooctyl 4-t-butylphthalate, diisooctyl 3-n-butylphthalate, diisooctyl 4-n-butylphthalate, diisooctyl 4,5-dimethylphthalate, diisooctyl 4,5-diethylphthalate, diisooctyl 4-methyl-5-ethyl phthalate, diisooctyl 4-methyl-5-t-butylphthalate, diisooctyl 4-ethyl-5-t-butylphthalate, di-n-decyl 4-methyl phthalate, diisodecyl 4-methylphthalate, di-n-decyl 4-ethyl phthalate, diisodecyl 4-ethylphthalate, ethyl-n-butyl 3-methylphthalate, ethyl-n-butyl 4-methylphthalate, ethyl-n-butyl 3-ethylphthalate, ethyl-n-butyl 4-ethylphthalate, ethyl-n-butyl 3-t-butylphthalate, ethyl-n-butyl 4-t-butyl phthalate, ethyl-n-butyl 4,5-dimethylphthalate, ethyl-n-butyl 4,5-diethylphthalate, ethyl-n-butyl 4-methyl-5-ethylphthalate, ethyl-n-butyl 4-ethyl-5-methylphthalate, ethylisobutyl 3-methylphthalate, ethylisobutyl 4-methyl phthalate, ethylisobutyl 3-ethylphthalate, ethylisobutyl 4-ethyl phthalate, ethylisobutyl 3-t-butylphthalate, ethyl isobutyl 4-t-butylphthalate, ethylisobutyl 4,5-dimethyl phthalate, ethyl isobutyl 4,5-diethylphthalate, ethyl isobutyl 4-methyl-5-ethylphthalate, ethylisobutyl 4-ethyl-5-methylphthalate, ethylisohexyl 3-methylphthalate, ethyl isohexyl 4-methylphthalate, ethylisohexyl 3-ethylphthalate, ethylisohexyl 4-ethylphthalate, ethylisohexyl 3-t-butyl phthalate, ethylisohexyl 4-t-butylphthalate, ethylisohexyl 4,5-dimethylphthalate, ethylisohexyl 4,5-diethylphthalate, ethylisohexyl 4-methyl-5-ethylphthalate, ethylisohexyl 4-ethyl-5-methylphthalate, n-butylisobutyl 3-methyl phthalate, n-butylisobutyl 4-methylphthalate, n-butyl isobutyl 3-ethylphthalate, n-butylisobutyl 4-ethylphthalate, n-butylisobutyl 3-t-butylphthalate, n-butylisobutyl 4-t-butylphthalate, n-butylisobutyl 4,5-dimethylphthalate, n-butylisobutyl 4,5-diethylphthalate, n-butylisobutyl 4-methyl-5-ethylphthalate, n-butylisobutyl 4-ethyl-5-methyl phthalate, n-butylisohexyl 3-methylphthalate, n-butyl isohexyl 4-methylphthalate, n-butylisohexyl 3-ethylphthalate, n-butylisohexyl 4-ethylphthalate, n-butylisohexyl 3-t-butyl phthalate, n-butylisohexyl 4-t-butylphthalate, n-butyl isohexyl 4,5-dimethylphthalate, n-butylisohexyl 4,5-diethyl phthalate, n-butylisohexyl 4-methyl-5-ethylphthalate, and n-butyl isohexyl 4-ethyl-5-methylphthalate.

Specific examples of the compounds of the above formula (1), wherein n=1 and $R^1$ is an alkyl group with 1 to 5 carbon atoms, or n=2 and $R^1$ is an alkyl group with 1 to 5 carbon atoms or a halogen atom, and one of the groups $R^2$ and $R^3$ is an alkyl group with 4 to 8 carbon atoms including a tertiary carbon atom include ethyl-t-butyl 3-methylphthalate, ethyl-t-butyl 4-methylphthalate, ethyl-t-butyl 3-ethylphthalate, ethyl-t-butyl 4-ethylphthalate, ethyl-t-butyl 4,5-dimethyl phthalate, ethyl-t-butyl 4,5-diethylphthalate, ethyl-t-butyl 4-methyl-5-ethylphthalate, ethyl-t-butyl 4-ethyl-5-methylphthalate, ethyl-t-butyl 4-methyl-5-chloro phthalate, ethyl-t-butyl 4-chloro-5-methylphthalate, ethyl-t-butyl 4-methyl-5-bromophthalate, ethyl-t-butyl 4-bromo-5-methylphthalate, ethyl-t-butyl 4-ethyl-5-chloro phthalate, ethyl-t-butyl 4-chloro-5-ethylphthalate, ethyl-t-butyl 4-ethyl-5-bromophthalate, ethyl-t-butyl 4-bromo-5-ethylphthalate, ethyl neopentyl 3-methylphthalate, ethylneopentyl 4-methylphthalate, ethyl-neopentyl 3-ethyl phthalate, ethylneopentyl 4-ethylphthalate, ethylneopentyl 4,5-dimethylphthalate, ethylneopentyl 4,5-diethylphthalate, ethylneopentyl 4-methyl-5-ethylphthalate, ethylneopentyl 4-ethyl-5-methylphthalate, ethylneopentyl 4-methyl-5-chlorophthalate, ethylneopentyl 4-chloro-5-methylphthalate, ethylneopentyl 4-methyl-5-bromophthalate, ethylneopentyl 4-bromo-5-methylphthalate, ethylneopentyl 4-ethyl-5-chloro phthalate, ethylneopentyl 4-chloro-5-ethylphthalate, ethyl neopentyl 4-ethyl-5-bromophthalate, ethylneopentyl 4-bromo-5-ethylphthalate, n-butylneopentyl 3-methylphthalate, n-butylneopentyl 4-methylphthalate, n-butylneopentyl 3-ethylphthalate, n-butylneopentyl 4-ethylphthalate, n-butylneopentyl 4,5-dimethylphthalate, n-butylneopentyl 4,5-diethylphthalate, n-butylneopentyl 4-methyl-5-ethyl phthalate, n-butylneopentyl 4-ethyl-5-methylphthalate, n-butylneopentyl 4-methyl-5-cllorophthalate, n-butyl neopentyl 4-chloro-5-methylphthalate, n-butylneopentyl 4-methyl-5-bromo phthalate, n-butylneopentyl 4-bromo-5-methylphthalate, n-butyl neopentyl 4-ethyl-5-chloro phthalate, n-butylneopentyl 4-chloro-5-ethylphthalate, n-butylneopentyl 4-ethyl-5-bromophthalate, and n-butyl neopentyl 4-bromo-5-ethylphthalate.

Specific examples of the compounds of the above formula (1), wherein n=1 or 2, $R^1$ is an alkyl group with 6 to 8 carbon atoms, and both $R^2$ and $R^3$ are alkyl groups with 4 to 8 carbon atoms including a tertiary carbon atom include di-t-butyl 4-n-hexylphthalate, di-t-butyl 4-isohexylphthalate, di-t-butyl 4-(2,2-dimethylbutyl) phthalate, di-t-butyl 4-(2,2-dimethylpentyl)phthalate, di-t-butyl isooctyl phthalate, di-t-butyl 4-n-hexyl-5-chlorophthalate, di-t-butyl 4-n-hexyl-5-bromophthalate, di-t-butyl 4-isohexyl-5-chlorophthalate, di-t-butyl 4-isohexyl-5-bromophthalate, di-t-butyl 4-(2,2-dimethylbutyl)-5-chlorophthalate, di-t-butyl 4-(2,2-dimethylbutyl)-5-bromophthalate, di-t-butyl 4-(2,2-dimethyl pentyl) phthalate, di-t-butyl isooctylphthalate, dineopentyl 4-n-hexylphthalate, dineopentyl 4-isohexylphthalate, dineopentyl 4-(2,2-dimethylbutyl) phthalate, dineopentyl 4-(2,2-dimethylpentyl)phthalate, dineopentyl isooctyl phthalate, dineopentyl 4-n-hexyl-5-chlorophthalate, dineopentyl 4-n-hexyl-5-bromophthalate, dineopentyl 4-isohexyl-5-chlorophthalate, dineopentyl 4-isohexyl-5-bromophthalate, dineopentyl 4-(2,2-dimethylbutyl)-5-chlorophthalate, dineopentyl 4-(2,2-dimethylbutyl)-5-bromophthalate, dineopentyl 4-(2,2-dimethylpentyl) phthalate, and dineopentyl isooctylphthalate.

Of these, preferable compounds are diethyl 4-methyl phthalate, di-n-butyl 4-methylphthalate, diisobutyl 4-methyl phthalate, diisohexyl 4-methylphthalate, diisooctyl 4-methyl phthalate, diethyl 4-ethylphthalate, di-n-butyl 4-ethyl phthalate, diisobutyl 4-ethylphthalate, diisohexyl 4-ethyl phthalate, diisooctyl 4-ethylphthalate, diethyl 4-t-butyl phthalate, di-n-butyl 4-t-butylphthalate, diisobutyl 4-t-butyl phthalate, diisohexyl 4-t-butylphthalate, diisooctyl 4-t-butylphthalate, diethyl 4,5-dimethylphthalate, di-n-butyl 4,5-dimethylphthalate, diisohexyl 4,5-dimethyl phthalate, diisooctyl 4,5-dimethylphthalate, diethyl 4,5-diethylphthalate, di-n-butyl 4,5-diethylphthalate, diisohexyl 4,5-diethylphthalate, diisooctyl 4,5-diethyl phthalate, diethyl 4-methyl-5-chlorophthalate, diethyl 4-methyl-5-bromophthalate, diethyl 4-ethyl-5-chloro phthalate, diethyl 4-ethyl-5-bromophthalate, di-n-butyl 4-methyl-5-chlorophthalate, di-n-butyl 4-methyl-5-bromo phthalate, di-n-butyl 4-ethyl-5-chlorophthalate, di-n-butyl 4-ethyl-5-bromophthalate, diisobutyl 4-methyl-5-chlorophthalate, diisobutyl 4-methyl-5-chlorophthalate, diisobutyl 4-methyl-5-bromophthalate, diisobutyl 4-ethyl-5-chlorophthalate, diisobutyl 4-ethyl-5-bromophthalate, diisohexyl 4-methyl-5-chlorophthalate, diisohexyl 4-methyl-5-bromophthalate, diisohexyl 4-ethyl-5-chlorophthalate, diisohexyl 4-ethyl-5-bromophthalate, diisooctyl 4-methyl-5-chlorophthalate, diisooctyl 4-methyl-5-bromophthalate, diisooctyl 4-ethyl-5-chloro phthalate, diisooctyl 4-ethyl-5-bromophthalate, and the like.

Specific examples of the compounds of the above formula (1), wherein n=1 or 2, $R^1$ is a halogen atom, and at least one of the groups $R^2$ or $R^3$ is an alkyl group with 1 to 12 carbon atoms other than the alkyl group with 4 to 8 carbon atoms including a tertiary carbon atom include diethyl 3-fluoro phthalate, diethyl 4-fluoro phthalate, diethyl 3-chloro phthalate, diethyl 4-chlorophthalate, diethyl 3-bromo phthalate, diethyl 4-bromophthalate, diethyl 3-iodophthalate, diethyl 4-iodophthalate, diethyl 4,5-dichloro phthalate, diethyl 4,5-dibromophthalate, diethyl 4-chloro-5-bromo phthalate, di-n-butyl 3-fluorophthalate, di-n-butyl 4-fluorophthalate, di-n-butyl 3-chlorophthalate, di-n-butyl 4-chlorophthalate, di-n-butyl 3-bromophthalate, di-n-butyl 4-bromophthalate, di-n-butyl 3-iodophthalate, di-n-butyl 4-iodophthalate, di-n-butyl 4,5-dichlorophthalate, di-n-butyl 4,5-dibromophthalate, di-n-butyl 4-chloro-5-bromo phthalate, diisobutyl 3-fluorophthalate, diisobutyl 4-fluorophthalate, diisobutyl 3-chlorophthalate, diisobutyl 4-chlorophthalate, diisobutyl 3-bromophthalate, diisobutyl 4-bromophthalate, diisobutyl 3-iodophthalate, diisobutyl 4-iodophthalate, diisobutyl 4,5-dichlorophthalate, diisobutyl 4,5-dibromophthalate, diisobutyl 4-chloro-5-bromophthalate, diisohexyl 3-fluorophthalate, diisohexyl 4-fluorophthalate, diisohexyl 3-chlorophthalate, diisohexyl 4-chlorophthalate, diisohexyl 3-bromophthalate, diisohexyl 4-bromophthalate, diisohexyl 3-iodophthalate, diisohexyl 4-iodophthalate, isohexyl 4,5-dichlorophthalate, diisohexyl 4,5-dibromophthalate, diisohexyl 4-chloro-5-bromophthalate, diisooctyl 3-fluorophthalate, diisooctyl 4-fluorophthalate, diisooctyl 3-chlorophthalate, diisooctyl 4-chlorophthalate, diisooctyl 3-bromophthalate, diisooctyl 4-bromophthalate, diisooctyl 3-iodophthalate, diisooctyl 4-iodophthalate, diisooctyl 4,5-dichlorophthalate, diisooctyl 4,5-dibromophthalate, diisooctyl 4-chloro-5-bromo phthalate, di-n-decyl 4-chlorophthalate, isodecyl 4-chloro phthalate, di-n-decyl 4-bromophthalate, isodecyl 4-bromo phthalate, ethyl-n-butyl 3-fluorophthalate, ethyl-n-butyl 4-fluorophthalate, ethyl-n-butyl 3-chlorophthalate, ethyl-n-butyl 4-chlorophthalate, ethyl-n-butyl 3-bromophthalate, ethyl-n-butyl 4-bromophthalate, ethyl-n-butyl 3-iodo phthalate, ethyl-n-butyl 4-iodophthalate, ethyl-n-butyl 4,5-dichlorophthalate, ethyl-n-butyl 4,5-dibromophthalate, ethyl-n-butyl 4-chloro-5-bromophthalate, ethylisobutyl 3-fluorophthalate, ethylisobutyl 4-fluorophthalate, ethylisobutyl 3-chlorophthalate, ethylisobutyl 4-chloro phthalate, ethylisobutyl 3-bromophthalate, ethylisobutyl 4-bromophthalate, ethylisobutyl 3-iodophthalate, ethyl isobutyl 4-iodophthalate, ethylisobutyl 4,5-dichloro phthalate, ethylisobutyl 4,5-dibromophthalate, ethyl isobutyl 4-chloro-5-bromophthalate, ethylisohexyl 3-fluorophthalate, ethylisohexyl 4-fluorophthalate, ethyl isohexyl 3-chlorophthalate, ethylisohexyl 4-chlorophthalate, ethylisohexyl 3-bromophthalate, ethylisohexyl 4-bromo phthalate, ethylisohexyl 3-iodophthalate, ethylisohexyl 4-iodophthalate, ethylisohexyl 4,5-dichlorophthalate, ethyl isohexyl 4,5-dibromophthalate, ethylisohexyl 4-chloro-5-bromophthalate, ethylisobutyl 3-fluorophthalate, ethyl isobutyl 4-fluorophthalate, ethylisobutyl 3-chlorophthalate, ethylisobutyl 4-chlorophthalate, ethylisobutyl 3-bromo phthalate, ethylisobutyl 4-bromophthalate, ethylisobutyl 3-iodophthalate, ethylisobutyl 4-iodophthalate, ethyl isobutyl 4,5-dichlorophthalate, ethylisobutyl 4,5-dibromo phthalate, ethylisobutyl 4-chloro-5-bromophthalate, n-butyl isobutyl 3-fluorophthalate, n-butylisobutyl 4-fluoro phthalate, n-butylisobutyl 3-chlorophthalate, n-butyl isobutyl 4-chlorophthalate, n-butyl isobutyl 3-bromophthalate, n-butylisobutyl 4-bromophthalate, n-butylisobutyl 3-iodo phthalate, n-butylisobutyl 4-iodophthalate, n-butylisobutyl 4,5-dichlorophthalate, n-butylisobutyl 4,5-dibromophthalate, n-butylisobutyl 4-chloro-5-bromophthalate, n-butylisohexyl 3-fluorophthalate, n-butylisohexyl 4-fluorophthalate, n-butylisohexyl 3-chlorophthalate, n-butylisohexyl 4-chlorophthalate, n-butylisohexyl 3-bromophthalate, n-butyl isohexyl 4-bromophthalate, n-butylisohexyl 3-iodophthalate, n-butylisohexyl 4-iodophthalate, n-butylisohexyl 4,5-dichlorophthalate, n-butylisohexyl 4,5-dibromophthalate, n-butylisohexyl 4-chloro-5-bromophthalate, ethyl-t-butyl 3-fluorophthalate, ethyl-t-butyl 4-fluorophthalate, ethyl-t-butyl 3-chlorophthalate, ethyl-t-butyl 4-chloro phthalate, ethyl-t-butyl 3-bromophthalate, ethyl-t-butyl 4-bromophthalate, ethyl-t-butyl 3-iodophthalate, ethyl-t-butyl 4-iodophthalate, ethyl-t-butyl 4,5-dichlorophthalate, ethyl-t-butyl 4,5-dibromophthalate, ethyl-t-butyl 4-chloro-5-bromophthalate, ethylneopentyl 3-fluorophthalate, ethyl neopentyl 4-fluorophthalate, ethylneopentyl 3-chloro phthalate, ethyl neopentyl 4-chlorophthalate, ethylneopentyl 3-bromophthalate, ethylneopentyl 4-bromophthalate, ethyl neopentyl 3-iodophthalate, ethylneopentyl 4-iodophthalate, ethylneopentyl 4,5-dichloro phthalate, ethylneopentyl 4,5-dibromophthalate, ethylneopentyl 4-chloro-5-bromo phthalate, n-butyl-t-butyl 3-fluorophthalate, n-butyl-t-butyl 4-fluorophthalate, n-butyl-t-butyl 3-chlorophthalate, n-butyl-t-butyl 4-chlorophthalate, n-butyl-t-butyl 3-bromo phthalate, n-butyl-t-butyl 4-bromophthalate, n-butyl-t-butyl 3-iodophthalate, n-butyl-t-butyl 4-iodophthalate, n-butyl-t-butyl 4,5-dichlorophthalate, n-butyl-t-butyl 4,5-dibromo phthalate, n-butyl-t-butyl 4-chloro-5-bromophthalate, n-butylneopentyl 3-fluorophthalate, n-butylneopentyl 4-fluorophthalate, n-butylneopentyl 3-chlorophthalate, n-butylneopentyl 4-chlorophthalate, n-butylneopentyl 3-bromophthalate, n-butylneopentyl 4-bromophthalate, n-butyl neopentyl 3-iodophthalate, n-butylneopentyl 4-iodophthalate, n-butylneopentyl 4,5-dichlorophthalate, n-butylneopentyl 4,5-dibromophthalate, and n-butylneopentyl 4-chloro-5-bromo phthalate.

Of these, preferable compounds are diethyl 4-bromo phthalate, di-n-butyl 4-bromophthalate, diisobutyl 4-bromo phthalate, diethyl 4-chlorophthalate, di-n-butyl 4-chloro phthalate, diisobutyl 4-chlorophthalate, diisohexyl 4-chloro phthalate, diisooctyl 4-chlorophthalate, diisohexyl 4-bromo phthalate, diisooctyl 4-bromophthalate, diethyl 4,5-dichloro phthalate, di-n-butyl 4,5-dichlorophthalate, isohexyl 4,5-dichlorophthalate, and diisooctyl 4,5-dichlorophthalate.

Among the above-described phthalic acid diester derivatives, particularly preferred compounds as an electron donor which is one of the components of the catalyst for the olefin polymerization are dineopentyl 4-methylphthalate, dineopentyl 3-fluorophthalate, dineopentyl 4,5-dimethyl phthalate, dineopentyl 4-bromophthalate, t-butylneopentyl phthalate, di-n-butyl 4-methylphthalate, di-n-butyl 4-t-butyl phthalate, diethyl 4-methylphthalate, diethyl 4-t-butyl phthalate, di-n-butyl 4-bromophthalate, di-n-butyl 4-chloro phthalate, di-n-butyl 4,5-dichlorophthalate, diisohexyl 4-bromophthalate, and dineopentyl 4-t-butylphthalate. These phthalic acid diesters derivatives may be used either individually or in combinations of two or more.

The phthalic acid diester derivatives of the present invention are useful as an electron donor of various olefin polymerization catalysts. Specifically, these phthalic acid diesters and their derivatives are useful as an electron donor of catalysts in the homo- or copolymerization of ethylene, propylene, 1-butene, 1-pentene, 4-methyl-1-pentene, vinyl cyclohexane, and the like, preferably in the homopolymerization of ethylene or propylene, or copolymerization of ethylene and propylene. In particular, these compounds are ideal as electron donors of catalysts used in the homopolymerization of propylene or the copolymerization of ethylene and propylene.

The phthalic acid diester derivatives of the present invention can be prepared by various methods. A most simple method is reacting a commercially available phthalate with an alkyl halide, followed by hydrolysis of the resulting product. A number of synthetic methods of esters are known as described, for example, in "Lecture of Experimental Chemistry" (the fourth edition, vol. 22). Some examples are described here. A most common ester synthetic method comprises an application of the dehydration reaction of a carboxylic acid and alcohol. A mineral acid such as hydrochloric acid and sulfuric acid or a base such as triethylamine may be used as a catalyst. Another well-known method comprises use of a dehydrating agent for the synthesis of esters. For example, dicyclohexyl carbodiimide, trifluoroacetic acid anhydride, and the like are used as the dehydrating agent. A synthetic method using a carboxylic acid anhydride instead of carboxylic acid is also known. Moreover, a method of synthesizing an ester from an acid halide is known. This method is commonly used for the esterification of a carboxylic acid with a low reactivity due to steric hindrance, for example. For synthesis of a carboxylic acid ester of a dibasic acid, a method of preparing an intermediate such as a mono-ester or half-ester, then obtaining a diester by directly esterifying this intermediate or via an acid halide is known. These methods and other known methods may be used.

In a specific synthesis method of dineopentyl 4-methyl phthalate, 4-methylphthalic acid and neopentyl alcohol are charged into a flask and refluxed for 2 hours in the presence of sulfuric acid. After completion of the reaction, the reaction mixture is allowed to cool to the room temperature, and distilled water and ether are added to the mixture to extract the reaction product into the ether layer. After repetition of a washing procedure of the ether layer by flushing, an aqueous solution of sodium hydrogen carbonate is added, followed by neutralization of the water layer. A salt solution is added and the washing procedure using distilled water is repeated. Sodium sulfate is then added to the ether layer, followed by filtration. Ether contained in the resulting filtrate is removed by vacuum distillation. Vacuum distillation is repeated to obtain a yellow liquid. The liquid is cooled and recrystallized from ethanol to obtain white crystals.

The phthalic acid diester derivative thus obtained can be identified by the nuclear magnetic resonance spectroscopy ($^1$H-NMR), Raman spectrometry, mass spectrometry (MS), and the like.

The use of the phthalic acid diester derivatives of the present invention as an electron donor of an olefin polymerization catalyst remarkably improves the polymerization activity, the yield of high stereoregularity polymers, and the response to hydrogen of the catalyst as compared with conventionally known high performance catalyst.

EXAMPLES

The present invention will be described in more detail by examples, which should not be construed as limiting the present invention.

Example 1

A 2.0 l three-necked flask equipped with a reflux condenser was charged with 25.0 g of 4-methyl phthalate and 100 g of neopentyl alcohol. 18 ml of sulfuric acid was slowly added at 66° C., followed by refluxing for two hours at 115 to 125° C. After cooling, the reaction solution was transferred to a separating funnel containing 150 ml of distilled water. The flask was washed with 200 ml of diethyl ether and the diethyl ether washing liquid was also poured into the separating funnel. After a flushing operation, an operation of removing the water layer (lower layer) was repeated three times. After the addition of 150 ml of a 5% aqueous solution of sodium hydrogen carbonate, a flushing operation was carried out to confirm that the water layer has a pH in the range of 7 to 8. After removing the water layer, the residue was washed with 300 ml of saturated brine and then with 150 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 13.0 g of a viscous yellow liquid was obtained at a column top temperature of 190° C. This liquid was cooled to about −10° C. to obtain white crystals, which were recrystallized from ethanol to obtain 11.8 g of highly pure white crystals (yield: 26.5%). As a result of analysis using the following MS analyzer, $^1$H-NMR analyzer, and Raman spectroscopic analyzer, the white crystals were identified to be dineopentyl 4-methyl phthalate. The results of the analyses are shown in Tables 1 to 3.

Analyzers

The Finigan Mat (GC-MS) was used for the MS analysis. The JEOL GSX270 and a $CDCl_3$ solvent were used for the $^1$H-NMR analysis. The JEOL RFT800 was used for the Raman spectroscopic analysis.

Example 2

A 2.0 l three-necked flask equipped with a reflux condenser was charged with 50.0 g of 4-bromophthalate and 100.1 g of neopentyl alcohol. 36 ml of sulfuric acid was slowly added at 69° C., followed by refluxing for three and a half hours at 115 to 125° C. After cooling, the reaction solution was transferred to a separating funnel containing 600 ml of distilled water. The flask was washed with 500 ml of diethyl ether and the diethyl ether washing liquid was also poured into the separating funnel. After a flushing operation, an operation of removing the water layer (lower layer) was repeated three times. After the addition of 250 ml of a 5% aqueous solution of sodium hydrogen carbonate, a flushing operation was carried out to confirm that the water layer has a pH in the range of 7 to 8. After removing the water layer, the residue was washed with 300 ml of saturated brine and then with 150 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 61.9 g of a viscous pale yellow liquid was obtained at a column top temperature of 170° C. This liquid was cooled to about −10° C. to obtain white crystals, which were recrystallized from ethanol to obtain 33.2 g of highly pure white crystals (yield: 39.2%). As a result of analysis carried out in the same manner as above, the white crystals were identified to be dineopentyl 4-bromophthalate. The results of the analyses are shown in Tables 1 to 3.

Example 3

A 2.0 l three-necked flask equipped with a reflux condenser was charged with 24.0 g of 3-fluorophthalate and 99.6 g of neopentyl alcohol. 18 ml of sulfuric acid was slowly added at 62° C., followed by refluxing for two hours at 115 to 125° C. After cooling, the reaction solution was transferred to a separating funnel containing 300 ml of distilled water. The flask was washed with 210 ml of diethyl ether and the diethyl ether washing liquid was also poured into the separating funnel. After a flushing operation, an operation of removing the water layer (lower layer) was repeated three times. After the addition of 150 ml of a 5% aqueous solution of sodium hydrogen carbonate, a flushing operation was carried out to confirm that the water layer has a pH in the range of 7 to 8. After removing the water layer, the residue was washed with 150 ml of saturated brine and then with 150 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 15.3 g of a viscous pale yellow liquid was obtained at a column top temperature of 150° C. This liquid was crystallized from ethanol to obtain 12.0 g of highly pure white crystals (yield: 28.4%). As a result of analysis carried out in the same manner as above, the white crystals were identified to be dineopentyl 3-fluorophthalate. The results of the analyses are shown in Tables 1 to 3.

Example 4

A 2.0 l three-necked flask equipped with a reflux condenser was charged with 21.1 g of 4,5-dimethyl phthalate and 99.7 g of neopentyl alcohol. 18 ml of sulfuric acid was slowly added at 67° C., followed by refluxing for two hours at 115 to 125° C. After cooling, the reaction solution was transferred to a separating funnel containing 300 ml of distilled water. The flask was washed with 210 ml of diethyl ether and the diethyl ether washing liquid was also poured into the separating funnel. After a flushing operation, an operation of removing the water layer (lower layer) was repeated three times. After the addition of 150 ml of a 5% aqueous solution of sodium hydrogen carbonate, a flushing operation was carried out to confirm that the water layer has a pH in the range of 7 to 8. After removing the water layer, the residue was washed with 150 ml of saturated brine and then with 100 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 18.9 g of a viscous yellow liquid was obtained at a column top temperature of 170° C. This liquid was crystallized from ethanol to obtain 12.1 g of highly pure white crystals (yield: 36.7%). As a result of analysis carried out in the same manner as above, the white crystals were identified to be dineopentyl 4,5-dimethyl phthalate. The results of the analyses are shown in Tables 1 to 3.

Example 5

A 2.0 l three-necked flask equipped with a reflux condenser was charged with 32.6 g of 4-tert-butyl phthalate and 150.0 g of neopentyl alcohol. 36 ml of sulfuric acid was slowly added at 66° C., followed by refluxing for three hours at 115 to 125° C. After cooling, the reaction solution was transferred to a separating funnel containing 400 ml of distilled water. The flask was washed with 300 ml of diethyl ether and the diethyl ether washing liquid was also poured into the separating funnel. After a flushing operation, an operation of removing the water layer (lower layer) was repeated three times. After the addition of 200 ml of a 5% aqueous solution of sodium hydrogen carbonate, a flushing operation was carried out to confirm that the water layer has a pH in the range of 7 to 8. After removing the water layer, the residue was washed with 200 ml of saturated brine and then with 150 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 23.6 g (yield: 44.3%) of a viscous yellow liquid was obtained at a column top temperature of 170° C. As a result of analysis carried out in the same manner as above, the yellow liquid was identified to be dineopentyl 4-tert-butyl phthalate. The results of the analyses are shown in Tables 1 to 3.

Example 6

Preparation of Solid Catalyst Component

A 500 ml round bottom flask equipped with a stirrer, of which the internal atmosphere had been sufficiently replaced by nitrogen gas, was charged with 10 g of diethoxymagnesium and 80 ml toluene to prepare a suspension. After the addition of 20 ml of titanium tetrachloride, the suspension was heated, and when the temperature increased to as high as 80° C., a solution prepared by dissolving 3.5 g of dineopentyl 4-methylphthalate obtained in Example 1 in 3.5 ml of toluene was added and the mixture was heated to 110° C. Then, the mixture was reacted for one hour while stirring at 110° C. After the reaction, the resulting reaction mixture was washed three times with 100 ml of toluene at 90° C. After the addition of 20 ml of titanium tetrachloride and 80 ml of toluene, the reaction mixture was heated to 110° C. and reacted for one hour while stirring. After the reaction, the resulting reaction mixture was washed seven times with 100 ml of n-heptane at 40° C., thereby obtaining a solid catalyst component. The liquid in the solid catalyst component was separated from the solid components by filtration and drying. The content of titanium in the solid components was determined to confirm that the content was 3.7 wt %.

Preparation of Polymerization Catalyst and Polymerization

A 2.0 l autoclave equipped with a stirrer, of which the internal atmosphere had been entirely replaced by nitrogen gas, was charged with 1.32 mmol of triethylaluminum, 0.13 mmol of cyclohexylmethyldimethoxysilane, and the above solid catalyst component (A) in an amount, in terms of the titanium atom contained therein, of 0.0026 mmol, thereby forming a polymerization catalyst. Then, with the addition of 2.0 l of hydrogen gas and 1.4 l of liquid propylene, the preliminary polymerization was carried out for 5 minutes at 20° C., following which the preliminary polymerization product was heated and the main polymerization was carried out for one hour at 70° C. The weight of the polymer (a) was 270.9 g and the weight of the polymer (b) insoluble in n-heptane determined by extracting this polymer for 6 hours in boiling n-heptane was 263.0 g. Thus, the proportion of the boiling n-heptane insoluble matters (hereinafter abbreviated as "HI") in the polymer was confirmed to be 97.5 wt %. The polymerization activity per 1 g of the solid catalyst component used was 60,100 g/g. The melt index (hereinafter abbreviated as "MI") of the polymer (a), determined by the test method according to ASTM D1238 or JIS K7210, was 19 g/10 min. The results are shown in Table 4. The polymerization activity per 1 g of the solid catalyst component used here was calculated by the following formula:

The polymerization activity=(a) 270.9 (g)/solid catalyst component 0.00451 (g)

Example 7

A solid catalyst component was prepared in the same manner as in Example 6, except for using a solution of 4.2 mg of dineopentyl 4-bromophthalate, prepared in Example 2, dissolved in 5.3 ml of toluene instead of the solution of 3.5 g of dineopentyl 4-methylphthalate in 3.5 ml of toluene. A polymerization catalyst was prepared from the solid catalyst component and polymerization was carried out using the catalyst. The content of titanium in the resulting solid catalyst component was 2.9 wt %. The polymerization activity of the solid catalyst component was 60,800 g/g, HI was 97.1 wt %, and MI was 25 g/10 min. The results of the polymerization are shown in Table 4.

Example 8

A solid catalyst component was prepared in the same manner as in Example 6, except for using a solution of 3.6 mg of dineopentyl 3-fluorophthalate, prepared in Example 3, dissolved in 4.7 ml of toluene instead of the solution of 3.5 g of dineopentyl 4-methylphthalate in 3.5 ml of toluene. A polymerization catalyst was prepared from the solid catalyst component and polymerization was carried out using the catalyst. The content of titanium in the resulting solid catalyst component was 3.2 wt %. The polymerization activity of the solid catalyst component was 58,000 g/g, HI was 96.9 wt %, and MI was 18 g/10 min. The results of the polymerization are shown in Table 4.

Example 9

Experiment With a Varied Amount of Hydrogen Using the Solid Catalyst Component of Example 6

The same experiment as in Example 6 was carried out, except for using 1.0 l of hydrogen instead of 2.0 l of hydrogen during polymerization. The polymerization activity of the solid catalyst component was 49,400 g/g, HI was 98.1 wt %, and MI was 6.6 g/10 min. The results of the polymerization are shown in Table 4.

Example 10

Experiment With a Varied Amount of Hydrogen Using the Solid Catalyst Component of Example 6

The same experiment as in Example 6 was carried out, except for using 3.0 l of hydrogen instead of 2.0 l of hydrogen during polymerization. The polymerization activity of the solid catalyst component was 60,000 g/g, HI was 96.3 wt %, and MI was 40 g/10 min. The results of the polymerization are shown in Table 4.

Example 11

Experiment With a Varied Amount of Hydrogen Using the Solid Catalyst Component of Example 6

The same experiment as in Example 6 was carried out, except for using 6.0 l of hydrogen instead of 2.0 l of hydrogen during polymerization. The polymerization activity of the solid catalyst component was 62,700 g/g, HI was 95.2 wt %, and MI was 140 g/10 min. The results of the polymerization are shown in Table 4.

Example 12

Experiment With a Varied Amount of Hydrogen Using the Solid Catalyst Component of Example 7

The same experiment as in Example 7 was carried out, except for using 1.0 l of hydrogen instead of 2.0 l of hydrogen during polymerization. The polymerization activity of the solid catalyst component was 50,100 g/g, HI was 97.7 wt %, and MI was 9.5 g/10 min. The results of the polymerization are shown in Table 4.

Example 13

Experiment With a Varied Amount of Hydrogen Using the Solid Catalyst Component of Example 7

The same experiment as in Example 7 was carried out, except for using 3.0 l of hydrogen instead of 2.0 l of hydrogen during polymerization. The polymerization activity of the solid catalyst component was 63,400 g/g, HI was 96.2 wt %, and MI was 47 g/10 min. The results of the polymerization are shown in Table 4.

Example 14

Experiment With a Varied Amount of Hydrogen Using the Solid Catalyst Component of Example 7

The same experiment as in Example 7 was carried out, except for using 6.0 l of hydrogen instead of 2.0 l of hydrogen during polymerization. The polymerization activity of the solid catalyst component was 64,700 g/g, HI was 94.4 wt %, and MI was 180 g/10 min. The results of the polymerization are shown in Table 4.

Comparative Example 1

A solid catalyst component was prepared in the same manner as in Example 6, except for using 3.3 ml of di-n-pentylphthalate instead of 3.5 g of dineopentyl 4-methyl phthalate. A polymerization catalyst was prepared from the solid catalyst component and polymerization was carried out using the catalyst. The content of titanium in the resulting solid catalyst component was 2.6 wt %. The polymerization activity of the solid catalyst component was 46,400 g/g, HI was 97.9 wt %, and MI was 10 g/10 min. The results of the polymerization are shown in Table 4.

Comparative Example 2

A solid catalyst component was prepared in the same manner as in Example 6, except for using 2.9 ml of di-n-butylphthalate instead of 3.5 g of dineopentyl 4-methylphthalate. A polymerization catalyst was prepared from the solid catalyst component and polymerization was carried out using the catalyst. The content of titanium in the resulting solid catalyst component was 3.0 wt %. The polymerization activity of the solid catalyst component was 42,400 g/g, HI was 98.7 wt %, and MI was 6.6 g/10 min. The results of the polymerization are shown in Table 4.

Comparative Example 3

Experiment With a Varied Amount of Hydrogen Using the Solid Catalyst Component of Comparative Example 1

The same experiment as in Comparative Example 1 was carried out, except for using 3.0 l of hydrogen instead of 2.0 l of hydrogen during polymerization. The polymerization activity of the solid catalyst component was 47,000 g/g, HI was 97.2 wt %, and MI was 24 g/10 min. The results of the polymerization are shown in Table 4.

Comparative Example 4

Experiment With a Varied Amount of Hydrogen Using the Solid Catalyst Component of Comparative Example 1

The same experiment as in Comparative Example 1 was carried out, except for using 6.0 l of hydrogen instead of 2.0 l of hydrogen during polymerization. The polymerization activity of the solid catalyst component was 48,200 g/g, HI was 96.8 wt %, and MI was 66 g/10 min. The results of the polymerization are shown in Table 4.

Comparative Example 5

Experiment With a Varied Amount of Hydrogen Using the Solid Catalyst Component of Comparative Example 2

The same experiment as in Comparative Example 2 was carried out, except for using 3.0 l of hydrogen instead of 2.0 l of hydrogen during polymerization. The polymerization activity of the solid catalyst component was 44,500 g/g, HI was 97.6 wt %, and MI was 16 g/10 min. The results of the polymerization are shown in Table 4.

Comparative Example 6

Experiment With a Varied Amount of Hydrogen Using the Solid Catalyst Component of Comparative Example 2

The same experiment as in Comparative Example 2 was carried out, except for using 6.0 l of hydrogen instead of 2.0 l of hydrogen during polymerization. The polymerization activity of the solid catalyst component was 47,500 g/g, HI was 97.2 wt %, and MI was 57 g/10 min. The results of the polymerization are shown in Table 4.

Example 15

A 2.0 l three-necked flask equipped with a reflux condenser was charged with 25.0 g of 4-methyl phthalate and 100 g of n-butyl alcohol. 18 ml of sulfuric acid was slowly added at 66° C., followed by refluxing for two hours at 115 to 125° C. After cooling, the reaction solution was transferred to a separating funnel containing 150 ml of distilled water. The flask was washed with 200 ml of diethyl ether and the diethyl ether washing liquid was also poured into the separating funnel. After a flushing operation, an operation of removing the water layer (lower layer) was repeated three times. After the addition of 150 ml of a 5% aqueous solution of sodium hydrogen carbonate, a flushing operation was carried out to confirm that the water layer has a pH in the range of 7 to 8. After removing the water layer, the residue was washed with 300 ml of saturated brine and then with 150 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 13.0 g of a viscous yellow liquid was obtained at a column top temperature of 190° C. This liquid was cooled to about −10° C. to obtain white crystals, which were recrystallized from ethanol to obtain 11.8 g of highly pure white crystals (yield: 26.5%). As a result of analysis using the following MS analyzer, $^1$H-NMR analyzer, and Raman spectroscopic analyzer, the white crystals were identified to be di-n-butyl 4-methyl phthalate. The results of the analyses are shown in Tables 1 to 3.

Example 16

A 2.0 l three-necked flask equipped with a reflux condenser was charged with 50.0 g of 4-bromophthalate and 100.1 g of n-butyl alcohol. 36 ml of sulfuric acid was slowly added at 69° C., followed by refluxing for three and a half hours at 115 to 125° C. After cooling, the reaction solution was transferred to a separating funnel containing 600 ml of distilled water. The flask was washed with 500 ml of diethyl ether and the diethyl ether washing liquid was also poured into the separating funnel. After a flushing operation, an operation of removing the water layer (lower layer) was repeated three times. After the addition of 250 ml of a 5% aqueous solution of sodium hydrogen carbonate, a flushing operation was carried out to confirm that the water layer has a pH in the range of 7 to 8. After removing the water layer, the residue was washed with 300 ml of saturated brine and then with 150 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 61.9 g of a viscous pale yellow liquid was obtained at a column top temperature of 170° C. This liquid was cooled to about −10° C. to obtain white crystals, which were recrystallized from ethanol to obtain 33.2 g of highly pure white crystals (yield: 39.2%). As a result of analysis carried out in the same manner as above, the white crystals were identified to be di-n-butyl 4-bromophthalate. The results of the analyses are shown in Tables 1 to 3.

Example 17

A 2.0 l three-necked flask equipped with a reflux condenser was charged with 32.6 g of 4-tert-butyl phthalate and 100.0 g of n-butyl alcohol. 36 ml of sulfuric acid was slowly added at 66° C., followed by refluxing for three hours at 115 to 125° C. After cooling, the reaction solution was transferred to a separating funnel containing 400 ml of distilled water. The flask was washed with 300 ml of diethyl ether and the diethyl ether washing liquid was also poured into the separating funnel. After a flushing operation, an operation of removing the water layer (lower layer) was repeated three times. After the addition of 200 ml of a 5% aqueous solution of sodium hydrogen carbonate, a flushing operation was carried out to confirm that the water layer has a pH in the range of 7 to 8. After removing the water layer, the residue was washed with 200 ml of saturated brine and then with 150 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 20.5 g (yield: 43.3%) of a viscous yellow liquid was obtained at a column top temperature of 170° C. As a result of analysis carried out in the same manner as above, the yellow liquid was identified to be di-n-butyl 4-t-butylphthalate. The results of the analyses are shown in Tables 1 to 3.

Example 18

A 2.0 l three-necked flask equipped with a reflux condenser was charged with 25.0 g of 4-methyl phthalate and 100 g of ethyl alcohol. 36 ml of sulfuric acid was slowly added at 66° C., followed by refluxing for three hours at 115 to 125° C. After cooling, the reaction solution was transferred to a separating funnel containing 400 ml of distilled water. The flask was washed with 300 ml of diethyl ether and the diethyl ether washing liquid was also poured into the separating funnel. After a flushing operation, an operation of removing the water layer (lower layer) was repeated three times. After the addition of 200 ml of a 5% aqueous solution of sodium hydrogen carbonate, a flushing operation was carried out to confirm that the water layer has a pH in the range of 7 to 8. After removing the water layer, the residue was washed with 200 ml of saturated brine and then with 150 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 12.5 g (yield: 37.5%) of a viscous yellow liquid was obtained at a column top temperature of 170° C. As a result of analysis carried out in the same manner as above, the yellow liquid was identified to be diethyl 4-methylphthalate. The results of the analyses are shown in Tables 1 to 3.

Example 19

A 2.0 l three-necked flask equipped with a reflux condenser was charged with 32.6 g of 4-tert-butyl phthalate and 100.0 g of ethyl alcohol. 36 ml of sulfuric acid was slowly added at 66° C., followed by refluxing for three hours at 115 to 125° C. After cooling, the reaction solution was transferred to a separating funnel containing 400 ml of distilled water. The flask was washed with 300 ml of diethyl ether and the diethyl ether washing liquid was also poured into the separating funnel. After a flushing operation, an operation of removing the water layer (lower layer) was repeated three times. After the addition of 200 ml of a 5% aqueous solution of sodium hydrogen carbonate, a flushing operation was carried out to confirm that the water layer has a pH in the range of 7 to 8. After removing the water layer, the residue was washed with 200 ml of saturated brine and then with 150 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 18.5 g (yield: 45.3%) of a viscous yellow liquid was obtained at a column top temperature of about 170° C. As a result of analysis carried out in the same manner as above, the yellow liquid was identified to be diethyl 4-t-butylphthalate. The results of the analyses are shown in Tables 1 to 3.

Example 20

A 2.0 l three-necked flask equipped with a reflux condenser was charged with 30.0 g of 4-chlorophthalate and 100 g of n-butyl alcohol. 36 ml of sulfuric acid was slowly added at 66° C., followed by refluxing for three hours at 115 to 125° C. After cooling, the reaction solution was transferred to a separating funnel containing 400 ml of distilled water. The flask was washed with 300 ml of diethyl ether and the diethyl ether washing liquid was also poured into the separating funnel. After a flushing operation, an operation of removing the water layer (lower layer) was repeated three times. After the addition of 200 ml of a 5% aqueous solution of sodium hydrogen carbonate, a flushing operation was carried out to confirm that the water layer has a pH in the range of 7 to 8. After removing the water layer, the residue was washed with 200 ml of saturated brine and then with 150 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 18.5 g (yield: 39.1%) of a viscous yellow liquid was obtained at a column top temperature of 170° C. As a result of analysis carried out in the same manner as above, the yellow liquid was identified to be di-n-butyl 4-chlorophthalate. The results of the analyses are shown in Tables 1 to 3.

Example 21

A 2.0 l three-necked flask equipped with a reflux condenser was charged with 33.0 g of 4,5-dichlorophthalate and 100 g of n-butyl alcohol. 36 ml of sulfuric acid was slowly added at 66° C., followed by refluxing for three hours at 115 to 125° C. After cooling, the reaction solution was transferred to a separating funnel containing 400 ml of distilled water. The flask was washed with 300 ml of diethyl ether and the diethyl ether washing liquid was also poured into the separating funnel. After a flushing operation, an operation of removing the water layer (lower layer) was repeated three times. After the addition of 200 ml of a 5% aqueous solution of sodium hydrogen carbonate, a flushing operation was carried out to confirm that the water layer has a pH in the range of 7 to 8. After removing the water layer, the residue was washed with 200 ml of saturated brine and then with 150 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 16.3 g (yield: 33.0%) of a viscous yellow liquid was obtained at a column top temperature of 170° C. As a result of analysis carried out in the same manner as above, the yellow liquid was identified to be di-n-butyl 4,5-dichlorophthalate. The results of the analyses are shown in Tables 1 to 3.

Example 22

A 2.0 l three-necked flask equipped with a reflux condenser was charged with 50.0 g of 4-bromophthalate and 100 g of isohexyl alcohol. 36 ml of sulfuric acid was slowly added at 66° C., followed by refluxing for three hours at 115 to 125° C. After cooling, the reaction solution was transferred to a separating funnel containing 400 ml of distilled water. The flask was washed with 300 ml of diethyl ether and the diethyl ether washing liquid was also poured into the separating funnel. After a flushing operation, an operation of removing the water layer (lower layer) was repeated three times. After the addition of 200 ml of a 5% aqueous solution of sodium hydrogen carbonate, a flushing operation was carried out to confirm that the water layer has a pH in the range of 7 to 8. After removing the water layer, the residue was washed with 200 ml of saturated brine and then with 150 ml of distilled water. The water layer was removed. The ether layer (upper layer) was transferred to an Erlenmeyer flask and dehydrated using anhydrous sodium sulfate. After removal of ether by distillation under reduced pressure, the residue was further distilled under reduced pressure. 35.5 g (yield: 42.1%) of a viscous yellow liquid was obtained at a column top temperature of 170° C. As a result of analysis carried out in the same manner as above, the yellow liquid was identified to be diisohexyl 4-bromophthalate. The results of the analyses are shown in Tables 1 to 3.

TABLE 1

| | | MS (Mw/z) | |
| --- | --- | --- | --- |
| Example | Compound Name | Molecular peak | Characteristic peak |
| 1 | dineopentyl 4-methylphthalate | 320 | 163 |
| 2 | dineopentyl 4-bromophthalate | 384, 386 | 184, 182 |
| 3 | dineopentyl 3-fluorophthalate | 324 | 167 |
| 4 | dineopentyl 4,5-dimethylphthalate | 334 | 177 |
| 5 | dineopentyl 4-t-butylphthalate | 362 | 205 |
| 15 | di-n-butyl 4-methylphthalate | 292 | 163 |
| 16 | di-n-butyl 4-bromophthalate | 356, 358 | 227, 229 |
| 17 | di-n-butyl 4-t-butylphthalate | 334 | 205 |

TABLE 1-continued

| | | MS (Mw/z) | |
|---|---|---|---|
| Example | Compound Name | Molecular peak | Characteristic peak |
| 18 | diethyl 4-methylphthalate | 236 | 163 |
| 19 | diethyl 4-t-butylphthalate | 278 | 205 |
| 20 | di-n-butyl 4-chlorophthalate | 312 | 183 |
| 21 | di-n-butyl 4,5-dichlorophthalate | 346, 348 | 217 |
| 22 | diisohexyl 4-bromophthalate | 412, 414 | 182, 184 |

TABLE 2

| | | $^1$H-NMR (ppm:Int) | | | |
|---|---|---|---|---|---|
| Example | Compound Name | Methyl al | Methyl ar | Methylene | Aromatic ring |
| 1 | dineopentyl 4-methylphthalate | 1.0s:18.1 | 2.4s:3.0 | 4.0s:4.0 | 7.3–7.7m:3.0 |
| 2 | dineopentyl 4-bromophthalate | 1.0s:18.0 | — | 4.0d:4.0 | 7.6–7.8m:3.0 |
| 3 | dineopentyl 3-fluorophthalate | 1.0d:18.0 | — | 4.0s:2.0<br>4.1s:2.0 | 7.3–7.8m:3.0 |
| 4 | dineopentyl 4,5-dimethylphthalate | 1.0s:18.0 | 2.4s:6.0 | 4.0s:4.0 | 7.6s:2.0 |
| 5 | dineopentyl 4-t-butylphthalate | 1.0d:18.0<br>1.3s:9.0 | — | 4.0d:4.0 | 7.3–7.8m:3.0 |
| 15 | di-n-butyl 4-methylphthalate | 1.0t:6.0 | 2.4s:3.0 | 1.4q:4.1<br>1.7m:4.0<br>4.3m:4.0 | 7.3–7.8m:3.0 |
| 16 | di-n-butyl 4-bromophthalate | 1.0td:6.1 | — | 1.4q:4.1<br>1.7m:4.1<br>4.3td:4.0 | 7.2–7.8m:2.9 |
| 17 | di-n-butyl 4-t-butylphthalate | 1.0t:6.0<br>1.3s:9.0 | — | 1.4m:4.0<br>1.7m:4.1<br>4.3t:4.0 | 7.3–7.8m:3.0 |
| 18 | diethyl 4-methylphthalate | 1.4t:6.0 | 2.4s:3.0 | 4.4q:4.0 | 7.9s:3.0 |
| 19 | diethyl 4-t-butylphthalate | 1.3s:9.0<br>1.4t:6.0 | — | 4.4q:4.0 | 7.3–7.8m:3.0 |
| 20 | di-n-butyl 4-chlorophthalate | 1.0t:6.0 | — | 1.4m:4.0<br>1.7m:4.0<br>4.3t:4.0 | 7.5–7.8m:3.0 |
| 21 | di-n-butyl 4,5-dichlorophthalate | 1.0t:6.0 | — | 1.4m:4.0<br>1.7m:4.0<br>4.3t:4.0 | 7.9s:2.0 |
| 22 | diisohexyl 4-bromophthalate | 0.9d:12.0 | — | 1.0–1.8m:2.1<br>1.3m:4.0<br>1.6m:3.9<br>3.6t:4.0 | 7.2–7.8m:3.0 |

TABLE 3

| | | Raman (cm$^{-1}$) | | | Elemental analysis (%) Found/Theoretical | | |
|---|---|---|---|---|---|---|---|
| Example | Compound Name | C=O | C-Car | Cal-H | C | H | O |
| 1 | dineopentyl 4-methylphthalate | 1724 | 1612 | 2963<br>2923 | 71.1/<br>71.2 | 8.8/<br>8.8 | 20.0/<br>20.0 |
| 2 | dineopentyl 4-bromophthalate | 1730 | 1593 | 2962<br>2940 | 56.1/<br>56.1 | 6.2/<br>6.5 | 16.6/<br>16.6 |
| 3 | dineopentyl 3-fluorophthalate | 1728 | 1610 | 2960<br>2908 | 66.7/<br>66.6 | 8.1/<br>7.8 | 20.2/<br>19.7 |
| 4 | dineopentyl 4,5-dimethylphthalate | 1720 | 1613 | 2965<br>2927 | 71.8/<br>71.8 | 8.9/<br>9.0 | 19.2/<br>19.1 |
| 5 | dineopentyl 4-t-butylphthalate | 1724 | 1612 | 2962<br>2918 | 72.8/<br>72.9 | 9.3/<br>9.5 | 17.8/<br>17.7 |
| 15 | di-n-butyl 4-methylphthalate | 1722 | 1608 | 2913<br>2873 | 69.8/<br>69.8 | 8.2/<br>8.2 | 20.7/<br>21.9 |
| 16 | di-n-butyl 4-bromophthalate | 1724 | 1589 | 2976<br>2937 | 54.1/<br>53.8 | 5.9/<br>5.9 | 15.7/<br>17.9 |

TABLE 3-continued

| Example | Compound Name | Raman (cm$^{-1}$) C=O | Raman (cm$^{-1}$) C-Car | Cal-H | Elemental analysis (%) Found/Theoretical C | H | O |
|---|---|---|---|---|---|---|---|
| 17 | di-n-butyl 4-t-butylphthalate | 1726 | 1606 | 2960 2908 | 71.8/ 71.8 | 9.0/ 9.0 | 18.9/ 19.1 |
| 18 | diethyl 4-methylphthalate | 1722 | 1610 | 2951 2911 | 66.2/ 66.1 | 6.7/ 6.8 | 27.1/ 27.1 |
| 19 | diethyl 4-t-butylphthalate | 1724 | 1606 | 2968 2937 | 68.8/ 69.0 | 8.1/ 8.0 | 22.9/ 23.0 |
| 20 | di-n-butyl 4-chlorophthalate | 1726 | 1593 | 2935 2907 2910 | 60.9/ 61.4 | 6.7/ 6.8 | 19.8/ 20.5 |
| 21 | di-n-butyl 4,5-dichlorophthalate | 1730 | 1589 | 2935 2911 2873 | 55.5/ 55.3 | 5.9/ 5.8 | 18.2/ 18.4 |
| 22 | diisohexyl 4-bromophthalate | 1724 | 1592 | 2971 2940 2871 | 57.9/ 58.1 | 7.2/ 7.1 | 19.1/ 19.3 |

TABLE 4

| | Compound Name | Amount of hydrogen (l) | Titanium content (wt %) | Polymerization activity (wt %) | HI (wt %) | MI (g/10 min.) |
|---|---|---|---|---|---|---|
| Example 6 | dineopentyl 4-methylphthalate | 2.0 | 2.8 | 60,100 | 97.5 | 19 |
| Example 7 | dineopentyl 4-bromophthalate | 2.0 | 2.9 | 60,800 | 97.1 | 25 |
| Example 8 | dineopentyl 3-fluorophthalate | 2.0 | 3.2 | 58,000 | 96.9 | 18 |
| Example 9 | dineopentyl 4-methylphthalate | 1.0 | 2.8 | 49,400 | 98.1 | 6.6 |
| Example 10 | dineopentyl 4-methylphthalate | 3.0 | 2.8 | 60,000 | 96.3 | 40 |
| Example 11 | dineopentyl 4-methylphthalate | 6.0 | 2.8 | 62,700 | 95.2 | 140 |
| Example 12 | dineopentyl 4-bromophthalate | 1.0 | 2.9 | 50,100 | 97.7 | 9.5 |
| Example 13 | dineopentyl 4-bromophthalate | 3.0 | 2.9 | 63,400 | 96.2 | 47 |
| Example 14 | dineopentyl 4-bromophthalate | 6.0 | 2.9 | 64,700 | 94.4 | 180 |
| Comparative Example 1 | di-n-pentyl phthalate | 2.0 | 2.6 | 46,400 | 97.9 | 10 |
| Comparative Example 2 | di-n-butyl phthalate | 2.0 | 3.0 | 42,400 | 98.7 | 6.6 |
| Comparative Example 3 | di-n-pentyl phthalate | 3.0 | 2.6 | 47,000 | 97.2 | 24 |
| Comparative Example 4 | di-n-pentyl phthalate | 6.0 | 2.6 | 48,200 | 96.8 | 66 |
| Comparative Example 5 | di-n-pentyl phthalate | 3.0 | 3.0 | 44,500 | 97.6 | 16 |
| Comparative Example 6 | di-n-pentyl phthalate | 6.0 | 3.0 | 47,500 | 97.0 | 57 |

Example 23

Preparation of Solid Catalyst Component (A)

A 500 ml round bottom flask equipped with a stirrer, of which the internal atmosphere had been sufficiently replaced by nitrogen gas, was charged with 10 g of diethoxy magnesium and 80 ml of toluene to prepare a suspension. After the addition of 20 ml of titanium tetrachloride, the suspension was heated, and when the temperature increased to as high as 80° C., 3.2 g of di-n-butyl 4-methylphthalate obtained in Example 15 was added and the mixture was heated to 110° C. Then, the mixture was reacted for one hour while stirring at 110° C. After the reaction, the resulting reaction mixture was washed three times with 100 ml of toluene at 90° C. After the addition of 20 ml of titanium tetrachloride and 80 ml of toluene, the reaction mixture was heated to 110° C. and reacted for one hour while stirring. After the reaction, the resulting reaction mixture was washed seven times with 100 ml of n-heptane at 40° C., thereby obtaining a solid catalyst component. The liquid in the solid catalyst component was separated from the solid components. The content of titanium in the solid components was determined to confirm that the content was 3.2 wt %.

Preparation of Polymerization Catalyst and Polymerization

The polymerization was carried out in the same manner as in Example 6. The results are shown in Table 5.

Example 24

A solid catalyst component was prepared in the same manner as in Example 23, except for using 3.7 g of di-n-butyl 4-t-butylphthalate prepared in Example 17 instead of 3.2 g of di-n-butyl 4-methylphthalate. A polymerization catalyst was prepared from the solid catalyst component and polymerization was carried out using the catalyst. The content of titanium in the resulting solid catalyst component was 3.3 wt %. The results of polymerization are also shown in Table 5.

Example 25

A solid catalyst component was prepared in the same manner as in Example 23, except for using 2.5 g of diethyl 4-methylphthalate prepared in Example 18 instead of 3.2 g of di-n-butyl 4-methylphthalate. A polymerization catalyst was prepared from the solid catalyst component and polymerization was carried out using the catalyst. The content of titanium in the resulting solid catalyst component was 3.1 wt %. The results of polymerization are also shown in Table 5.

Example 26

A solid catalyst component was prepared in the same manner as in Example 23, except for using 3.0 g of diethyl 4-t-butylphthalate prepared in Example 19 instead of 3.2 g of di-n-butyl 4-methylphthalate. A polymerization catalyst was prepared from the solid catalyst component and polymerization was carried out using the catalyst. The content of titanium in the resulting solid catalyst component was 3.4 wt %. The results of polymerization are also shown in Table 5.

Example 27

Using a solid catalyst component obtained in the same manner as in Example 23, a polymerization catalyst was prepared in the same manner as in Example 6, except that 0.13 mmol of dicyclopentyldimethoxysilane (DCPDMS) was used as an organic silicon compound instead of 0.13 mmol of the cyclohexylmethyldimethoxysilane (CMDMS). The results of polymerization are also shown in Table 5.

Example 28

Using a solid catalyst component obtained in the same manner as in Example 23, a polymerization catalyst was prepared in the same manner as in Example 6, except that 0.13 mmol of diisopropyldimethoxysilane (DCPDMS) was used as an organic silicon compound instead of 0.13 mmol of the cyclohexylmethyldimethoxysilane (CMDMS). The results of polymerization are also shown in Table 5.

Comparative Example 7

Using a solid catalyst component obtained in the same manner as in Comparative Example 2, a polymerization catalyst was prepared in the same manner as in Comparative Example 1, except that 0.13 mmol of dicyclopentyldimethoxysilane (DCPDMS) was used as an organic silicon compound instead of 0.13 mmol of the cyclohexylmethyldimethoxysilane (CMDMS). The results of polymerization are also shown in Table 5.

Comparative Example 8

Using a solid catalyst component obtained in the same manner as in Comparative Example 2, a polymerization catalyst was prepared in the same manner as in Comparative Example 1, except that 0.13 mmol of diisopropyldimethoxysilane (DCPDMS) was used as an organic silicon compound instead of 0.13 mmol of the cyclohexylmethyldimethoxysilane (CMDMS). The results of polymerization are also shown in Table 5.

TABLE 5

| | Polymerization activity (g/g-cat.) | HI (wt %) | MI (g/10 min) | Organic silicon compound |
|---|---|---|---|---|
| Example 23 | 50,300 | 98.6 | 14 | CMDMS |
| Example 24 | 47,200 | 98.0 | 17 | CMDMS |
| Example 25 | 52,000 | 98.9 | 13 | CMDMS |
| Example 26 | 47,900 | 98.3 | 13 | CMDMS |
| Example 27 | 57,100 | 99.1 | 7.0 | DCPDMS |
| Example 28 | 53,200 | 98.9 | 11 | DIPDMS |
| Comparative Example 7 | 52,900 | 99.1 | 3.6 | DCPDMS |
| Comparative Example 8 | 47,500 | 98.7 | 6.8 | DIPDMS |

Example 29

Preparation of Solid Catalyst Component (A)

A 500 ml round bottom flask equipped with a stirrer, of which the internal atmosphere had been sufficiently replaced by nitrogen gas, was charged with 10 g of diethoxymagnesium and 80 ml toluene to prepare a suspension. After the addition of 20 ml of titanium tetrachloride, the suspension was heated, and when the temperature increased to as high as 80° C., 3.9 g of di-n-butyl 4-bromophthalate obtained in Example 16 was added and the mixture was heated to 110° C. Then, the mixture was reacted for one hour while stirring at 110° C. After the reaction, the resulting reaction mixture was washed three times with 100 ml of toluene at 90° C. After the addition of 20 ml of titanium tetrachloride and 80 ml of toluene, the reaction mixture was heated to 110° C. and reacted for one hour while stirring. After the reaction, the resulting reaction mixture was washed seven times with 100 ml of n-heptane at 40° C., thereby obtaining a solid catalyst component. The liquid in the solid catalyst component was separated from the solid components. The content of titanium in the solid components was determined to confirm that the content was 2.6 wt %.

Preparation of Polymerization Catalyst and Polymerization

The polymerization was carried out in the same manner as in Example 6. The results are shown in Table 6.

Example 30

A solid catalyst component was prepared in the same manner as in Example 1, except for using 3.2 g of di-n-butyl 4-chlorophthalate prepared in Example 20 instead of 3.9 g of di-n-butyl 4-bromophthalate. A polymerization catalyst was prepared from the solid catalyst component and polymerization was carried out using the catalyst. The content of titanium in the resulting solid catalyst component was 3.3 wt %. The results of polymerization are also shown in Table 6.

Example 31

A solid catalyst component was prepared in the same manner as in Example 1, except for using 3.8 g of di-n-butyl 4,5-dichlorophthalate prepared in Example 21 instead of 3.9 g of di-n-butyl 4-bromophthalate. A polymerization catalyst was prepared from the solid catalyst component and polymerization was carried out using the catalyst. The content of titanium in the resulting solid catalyst component was 3.0 wt %. The results of polymerization are also shown in Table 6.

Example 32

A solid catalyst component was prepared in the same manner as in Example 1, except for using 4.5 g of diisohexyl 4-bromophthalate prepared in Example 22 instead of 3.9 g of di-n-butyl 4-bromophthalate. A polymerization catalyst was prepared from the solid catalyst component and polymerization was carried out using the catalyst. The content of titanium in the resulting solid catalyst component was 2.9 wt %. The results of polymerization are also shown in Table 6.

Example 33

Using a solid catalyst component obtained in the same manner as in Example 29, a polymerization catalyst was prepared in the same manner as in Example 6, except that 0.13 mmol of dicyclopentyldimethoxysilane (DCPDMS) was used as an organic silicon compound instead of 0.13 mmol of the cyclohexylmethyldimethoxysilane (CMDMS). The results of polymerization are also shown in Table 6.

Example 34

Using a solid catalyst component obtained in the same manner as in Example 29, a polymerization catalyst was prepared in the same manner as in Example 6, except that 0.13 mmol of diisopropyldimethoxysilane (DCPDMS) was used as an organic silicon compound instead of 0.13 mmol of the cyclohexylmethyldimethoxysilane (CMDMS). The results of polymerization are also shown in Table 6.

TABLE 6

|  | Polymerization activity (g/g-cat.) | HI (Wt %) | MI (g/10 min) | Organic silicon compound |
| --- | --- | --- | --- | --- |
| Example 29 | 49,800 | 98.5 | 13 | CMDMS |
| Example 30 | 47,200 | 98.2 | 15 | CMDMS |
| Example 31 | 43,900 | 97.9 | 21 | CMDMS |
| Example 32 | 49,400 | 98.0 | 18 | CMDMS |
| Example 33 | 54,400 | 99.0 | 7.5 | DCPDMS |
| Example 34 | 53,500 | 98.8 | 12 | DIPDMS |

As can be seen from the results of Tables 4, 5, and 6, olefin polymers can be obtained at an extremely high yield by polymerizing olefins using the catalyst containing the phthalic acid diester derivatives of the present invention as an electron donor. In addition, the polymers of the Examples have a higher MI value as compared with the polymers of the Comparative Examples, indicating a higher response to hydrogen of the catalyst.

INDUSTRIAL APPLICABILITY

As mentioned above, the phthalic acid diester derivatives of the present invention remarkably improves the polymerization activity, increases the yield of high stereoregularity polymers, and promotes the response to hydrogen of the catalyst if used as an electron donor of an olefin polymerization catalyst as compared with conventionally known high performance catalyst. The catalyst is thus expected not only to produce polyolefins for common use at a low cost, but also to be useful in the manufacture of copolymer olefins having high functions.

What is claimed is:

1. A phthalic acid diester derivative of the following formula (1),

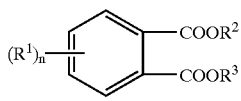

(1)

wherein $R^1$ is an alkyl group having 1 to 8 carbon atoms or a halogen atom; $R^2$ and $R^3$ may be either identical or different, representing an alkyl group having 1 to 12 carbon atoms; and n, which indicates the number of $R^1$, is 1 or 2, provided that when n is 2, the two groups may be either identical or different, provided further that at least one of the groups or $R^3$ is an alkyl group having a tertiary carbon atom and containing 4 to 8 carbon atoms.

2. The phthalic acid diester derivative according to claim 1, having the formula (1) wherein n=1 and $R^1$ is a methyl group or a tert-butyl group, or n=2 and at least one of the groups $R^1$ is a methyl group or a tert-butyl group.

3. The phthalic acid diester derivative according to claim 1, having the formula (1) wherein $R^1$ is a chlorine atom, a bromine atom, or a fluorine atom.

4. The phthalic acid diester derivative according to claim 1, having the formula (1) wherein the group $R^1$ replaces the hydrogen atom at least one of the 4 and 5 positions of the benzene ring.

5. The phthalic acid diester derivative according to claim 1, having the formula (1) wherein at least one of the groups $R^2$ or $R^3$ is a neopentyl group or a tert-butyl group.

6. The phthalic acid diester derivative according to claim 1, wherein the phthalic acid diester derivative is dineopentyl 4-methylphthalate, dineopentyl 4,5-dimethylphthalate, dineopentyl 4-bromophthalate, dineopentyl 3-fluorophthalate, or dineopentyl 4-t-butyl phthalate.

7. The phthalic acid diester derivative according to claim 1, wherein $R^2$ is a neopentyl group.

8. The phthalic acid diester derivative according to claim 1, wherein $R^3$ is a neopentyl group.

9. The phthalic acid diester derivative according to claim 1, wherein $R^2$ is a tert-butyl group.

10. The phthalic acid diester derivative according to claim 1, wherein $R^3$ is a tert-butyl group.

11. The phthalic acid diester derivative according to claim 1, wherein the phthalic acid diester derivative is dineopentyl 4-methylphthalate.

12. The phthalic acid diester derivative according to claim 1, wherein the phthalic acid diester derivative is dineopentyl 4,5-dimethylphthalate.

13. The phthalic acid diester derivative according to claim 1, wherein the phthalic acid diester derivative is dineopentyl 4-bromophthalate.

14. The phthalic acid diester derivative according to claim 1, wherein the phthalic acid diester derivative is dineopentyl 3-fluorophthalate.

15. The phthalic acid diester derivative according to claim 1, wherein the phthalic acid diester derivative is dineopentyl 4-t-butyl phthalate.

16. The phthalic acid diester derivative according to claim 1, wherein n is 1.

17. The phthalic acid diester derivative according to claim 1, wherein n is 2.

18. The phthalic acid diester derivative according to claim 1, wherein n=1 and $R^1$ is a methyl group or a tert-butyl group.

19. The phthalic acid diester derivative according to claim 1, wherein n=2 and at least one of the groups $R^1$ is a methyl group or a tert-butyl group.

* * * * *